(12) United States Patent
Normand et al.

(10) Patent No.: US 6,406,276 B1
(45) Date of Patent: Jun. 18, 2002

(54) CONSTANT-PRESSURE FLUID SUPPLY SYSTEM WITH MULTIPLE FLUID CAPABILITY

(75) Inventors: Gerard B. Normand, Manchester, NH (US); Kevin Durand, Lancaster, MA (US); Joseph B. Seale, Gorham, ME (US); Dean L. Kamen, Bedford, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 07/855,176

(22) Filed: Mar. 20, 1992

Related U.S. Application Data

(63) Continuation-in-part of application No. 07/748,346, filed on Aug. 22, 1991, now abandoned, which is a continuation-in-part of application No. 07/673,835, filed on Mar. 22, 1991, now abandoned, which is a continuation-in-part of application No. 07/615,612, filed on Nov. 19, 1990, now abandoned, and a continuation-in-part of application No. 07/614,806, filed on Nov. 19, 1990, now abandoned, which is a continuation-in-part of application No. 07/523,801, filed on May 15, 1990, now Pat. No. 5,088,515, and a continuation-in-part of application No. 07/345,387, filed on May 1, 1989, now Pat. No. 4,976,162, which is a continuation-in-part of application No. 07/092,481, filed on Sep. 3, 1987, now Pat. No. 4,826,482, which is a continuation-in-part of application No. 07/022,167, filed on Mar. 5, 1987, now Pat. No. 4,808,161, and a continuation-in-part of application No. 06/836,023, filed on Mar. 4, 1986, now Pat. No. 4,778,451.

(51) Int. Cl.⁷ .............................................. F04B 43/06
(52) U.S. Cl. ...................................................... 417/395
(58) Field of Search ................................ 417/394, 395, 417/349, 437, 478, 479

(56) References Cited

U.S. PATENT DOCUMENTS 1,389,635 A * 9/1921 Dunkle ....................... 417/395
1,771,424 A 7/1930 Steurs ......................... 604/81

(List continued on next page.)

FOREIGN PATENT DOCUMENTS

| DE | 27 31 448 | 1/1978 |
| DE | 36 05 664 | 8/1987 |
| EP | 380862 | 8/1990 |
| WO | 88/03819 | 6/1988 |

OTHER PUBLICATIONS

"vs. Pharmacy Control," Baxter, Date Unknown.
"Travenol Infusor Chemotherapy," Travenol, Feb. 1987.

(List continued on next page.)

*Primary Examiner*—Charles G. Freay
(74) *Attorney, Agent, or Firm*—Bromberg & Sunstein LLP

(57) ABSTRACT

The invention provides a system for dispensing fluid at relatively constant pressure. In a first embodiment, the invention dispenses a fluid from a chamber of varying dimension defined by a pre-tensioned resilient membrane. In a second embodiment, the invention dispenses a fluid from a chamber defined by a dispensing membrane, which is substantially surrounded by another fluid contained within a pressure chamber of varying dimension defined by a pre-tensioned resilient membrane. In a third embodiment, the invention dispenses multiple fluids, a first fluid from a first dispensing chamber of varying dimension defined by a pre-tensioned resilient membrane, and a second fluid from a dispensing chamber of varying dimension defined by a dispensing membrane substantially surrounded by the first fluid. In a fourth embodiment the invention dispenses multiple fluids from at least two dispensing chambers of varying dimension each substantially surrounded by the pressure fluid contained within a pressure chamber of varying dimension defined by a pre-tensioned resilient membrane. In a preferred embodiment, the resilient membrane is pre-tensioned beyond the point at which, as fluid enters the volume contained by the membrane and the volume increases, the first derivative of pressure over volume becomes zero for the first time.

42 Claims, 6 Drawing Sheets

U.S. PATENT DOCUMENTS

| | | | | |
|---|---|---|---|---|
| 2,740,259 A | * | 4/1956 | Westlund | 417/395 |
| 2,970,749 A | * | 2/1961 | Montague | 417/478 |
| 3,046,903 A | * | 7/1962 | Jones | 417/478 |
| 3,148,624 A | * | 9/1964 | Baldwin | 417/394 |
| 3,335,666 A | | 8/1967 | Czarnecki | 103/44 |
| 3,468,308 A | | 9/1969 | Bierman | 128/214 |
| 3,469,578 A | | 9/1969 | Bierman | 128/214 |
| 3,506,005 A | | 4/1970 | Gilio et al. | 128/214 |
| 3,515,640 A | * | 6/1970 | Rudlin | 417/394 |
| 3,586,462 A | | 6/1971 | Kaiser et al. | 417/394 |
| 3,677,444 A | | 7/1972 | Merrill | 222/135 |
| 3,722,756 A | | 3/1973 | Cramer, Jr. | 222/212 |
| 3,993,069 A | | 11/1976 | Buckles et al. | 128/214 F |
| 4,116,589 A | * | 9/1978 | Rishton | 417/394 |
| 4,269,906 A | * | 5/1981 | Schmechtig | 92/90 |
| 4,413,952 A | * | 11/1983 | Burnham | 417/394 |
| 4,419,096 A | | 12/1983 | Leeper et al. | 604/132 |
| 4,429,540 A | * | 2/1984 | Burnham | 417/394 |
| 4,634,430 A | * | 1/1987 | Polaschegg | 417/395 |
| 4,968,301 A | | 11/1990 | di Palma et al. | 604/132 |
| 5,080,652 A | | 1/1992 | Sancoff et al. | 604/132 |
| 5,167,631 A | | 12/1992 | Thompson et al. | 604/132 |

OTHER PUBLICATIONS

"The Homepump Family of Disposable Elastomeric Infusion Systems," McGaw, Date Unknown.

"Intermate," Infusion Systems Corporation, Date Unknown.

"Home Pump—Disposable Elastomeric Infusion System," Block Medical, Inc. (Nov. 1990).

"Three easy steps to more convenient SASH," Block Medical, Inc. (1991).

* cited by examiner

CONSTANT-PRESSURE FLUID SUPPLY SYSTEM WITH MULTIPLE FLUID CAPABILITY

This application is a continuation in part of U.S. application Ser. No. 07/748,346, filed Aug. 22, 1991, now abandoned, which is a continuation in part of application Ser. No. 07/673,835, filed Mar. 22, 1991, now abandoned entitled "Constant Pressure Fluid Supply System," which is a continuation in part of applications Ser. No. 07/615,612, filed Nov. 19, 1990, now abandoned, and Ser. No. 07/614,806, filed Nov. 19, 1990, now abandoned, which are continuations in part of applications Ser. No. 07/523,801, filed May 15, 1990 issued Feb. 18, 1992 as U.S. Pat. No. 5,088,515 and Ser. No. 07/345,387, filed May 1, 1989, issued Dec. 11, 1990 as U.S. Pat. No. 4,976,162, which is a continuation in part of application Ser. No. 07/092,481, filed Sep. 3, 1987, issued as U.S. Pat. No. 4,826,482, which is a continuation in part of applications Ser. No. 07/022,167, filed Mar. 5, 1987, issued as U.S. Pat. No. 4,808,161, and Ser. No. 06/836,023, filed Mar. 4, 1986, issued as U.S. Pat. No. 4,778,451. These related applications are hereby incorporated herein by reference.

TECHNICAL FIELD

The present invention relates generally to systems for supplying and controlling fluid flow, and in particular to medical infusion technology, although other embodiments are possible.

SUMMARY OF THE INVENTION

The invention provides a system for dispensing fluid at relatively constant pressure. In a first embodiment, the invention dispenses a fluid from a chamber of varying dimension defined by a pre-tensioned resilient membrane. In a second embodiment, the invention dispenses a fluid from a chamber defined by a dispensing membrane, which is substantially surrounded by another fluid contained within a pressure chamber of varying dimension defined by a pre-tensioned resilient membrane. In a third embodiment, the invention dispenses multiple fluids, a first fluid from a first dispensing chamber of varying dimension defined by a pre-tensioned resilient membrane, and a second fluid from a dispensing chamber of varying dimension defined by a dispensing membrane substantially surrounded by the first fluid. In a fourth embodiment the invention dispenses multiple fluids from at least two dispensing chambers of varying dimension each substantially surrounded by the pressure fluid contained within a pressure chamber of varying dimension defined by a pre-tensioned resilient membrane.

In a preferred embodiment, the resilient membrane is pre-tensioned beyond the point at which, as fluid enters the volume contained by the membrane and the volume increases, the first derivative of pressure over volume becomes zero for the first time.

BRIEF DESCRIPTION OF THE DRAWINGS

The invention will be more readily understood by reference to the following description taken with the accompanying drawings in which.

DETAILED DESCRIPTION OF SPECIFIC EMBODIMENTS

Figure 1:
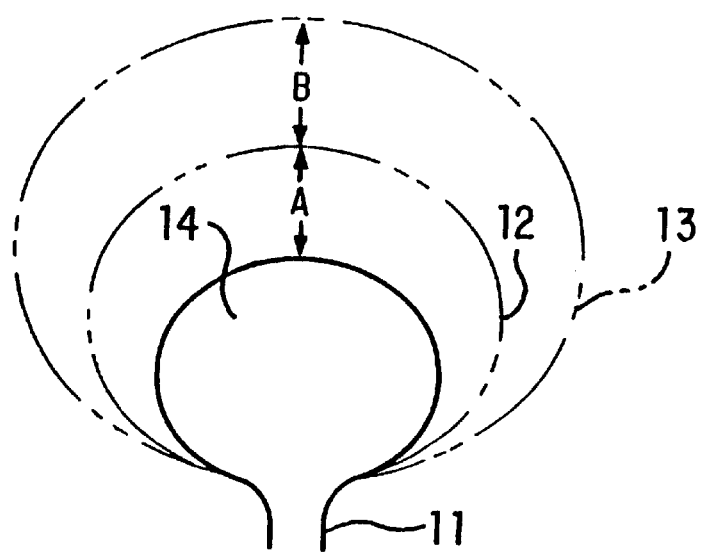
FIGS. 1 and 2 illustrate the characteristics of a resilient membrane of the type used in the invention.

FIG. 1 illustrates the use of a resilient membrane 11 of the type suitable for embodiments of the present invention. A membrane of substantially uniform thickness when filled to a requisite degree of fluid will tend to assume a spherical shape. Although any initial shape is possible, the membrane shown here is assumed to be substantially spherical in shape prior to any substantial amount of stretching caused by the introduction of fluid into the interior volume 14 of the membrane. As additional fluid is introduced into the membrane, its shape grows larger and reaches extents indicated by 12 and thereafter 13 in FIG. 1. Until fluid has substantially filled the volume 14 of membrane 11 (or more precisely until pressure inside the volume 14 exceeds ambient pressure), the membrane is not stretched. However, at some point fluid cannot be introduced into volume 14 without causing stretching of the walls of the membrane 11 and the consequent increase in pressure in the volume 14 within the membrane.

Figure 2:
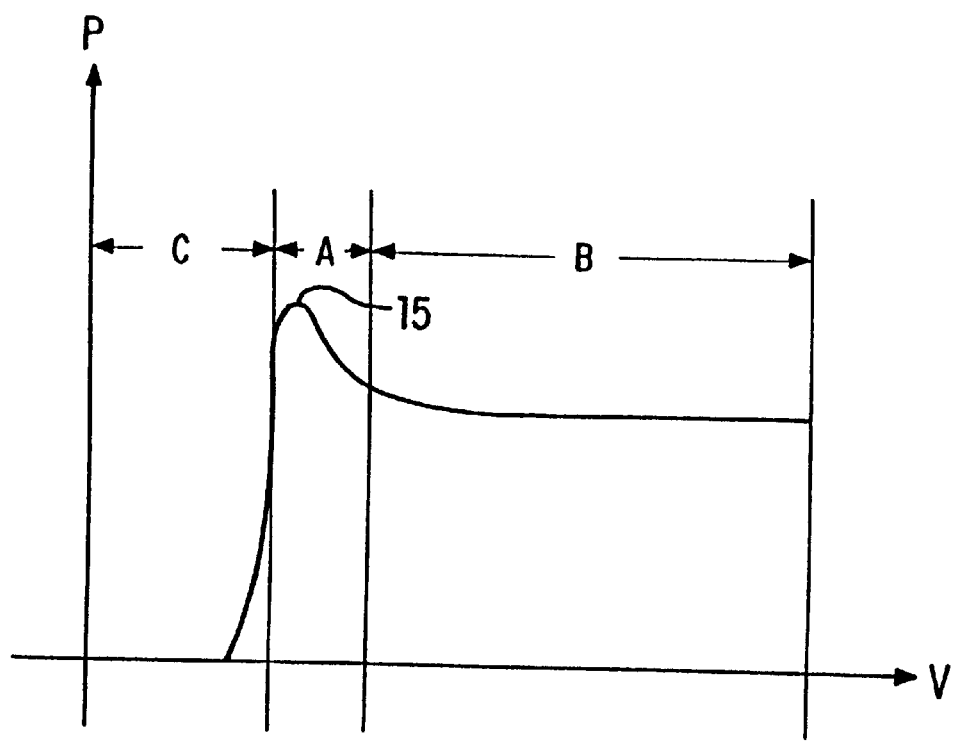

FIG. 2 illustrates the pressure versus volume characteristics of the resilient membrane shown in FIG. 1. To achieve initial growth in volume—in the region identified as region A in FIGS. 1 and 2—a comparatively large pressure is required to initiate the stretching of the membrane that is necessary to increase the volume 14 within it. Once the initial stretching has occurred, however, over a substantial volume range indicated by region B in FIGS. 1 and 2, the pressure tends to remain substantially constant. There is a point at which, as fluid enters the volume contained by the resilient membrane and the volume increases, the first derivative of pressure over volume becomes zero for the first time (15 in FIG. 2). At some point, of course, the membrane will enter a condition under which it has been stretched beyond its ability to maintain these characteristics and is subject to breakage. Region B is defined not to extend to that condition.

Typically delivery systems of the general type to which the invention is applicable must cope with the characteristics described in FIGS. 1 and 2. They typically operate in regions A and B in the course of delivery of intravenous fluids. In fact, near the end of the delivery cycle, as the volume 14 of membrane 11 reaches its initial size, the pressure-volume relationship is in fact in the region identified as C in FIG. 2, and the pressure drops precipitously to zero before all the fluid has been delivered, leaving some fluid still remaining in the device.

Figure 3:
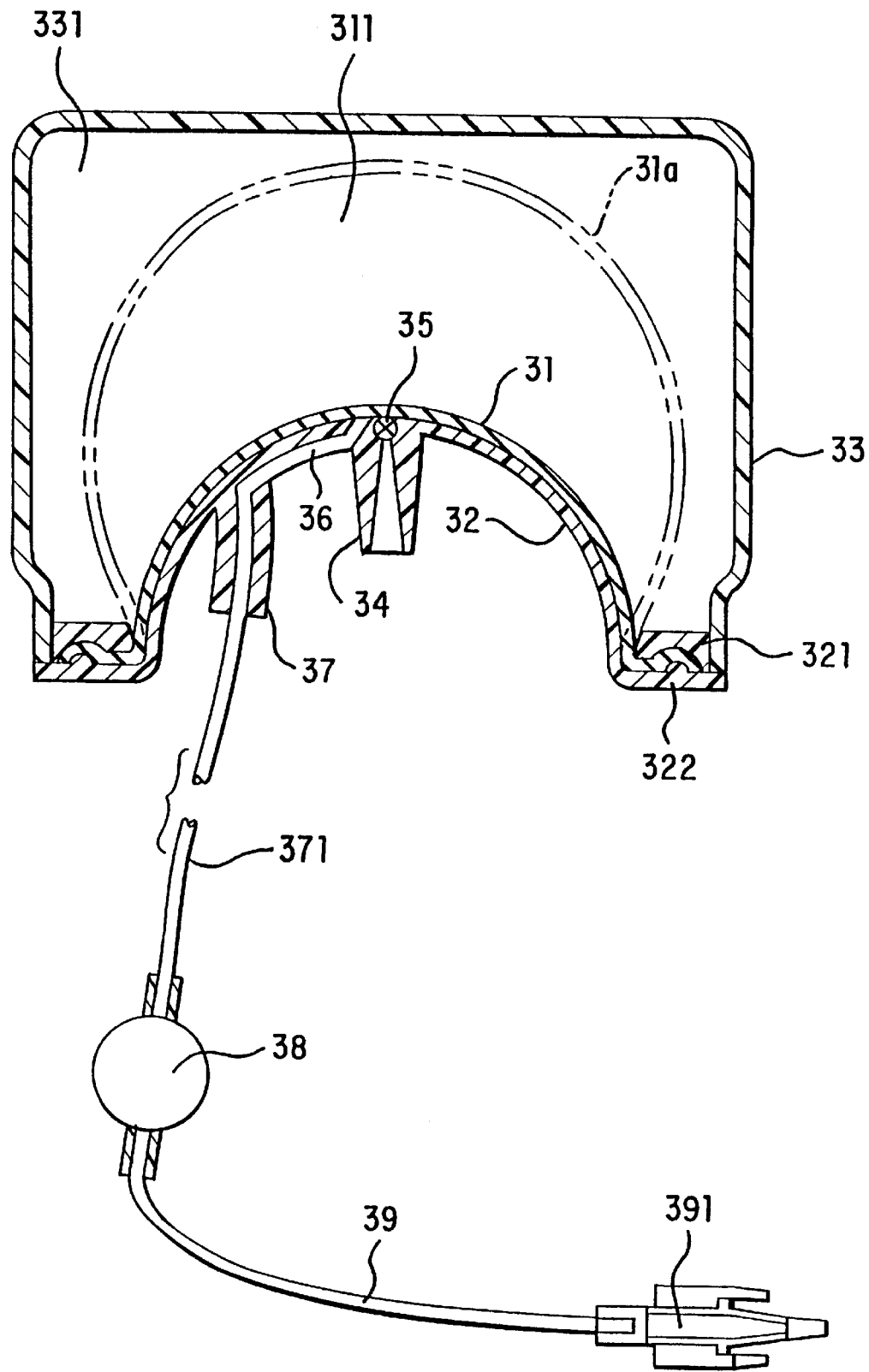
FIG. 3 shows a cross section of a first embodiment of the invention.

The present invention solves the problems posed in delivery systems of this type by providing an arrangement for mounting a resilient membrane under tension in such a way that the membrane operates only in the region B of FIG. 2. In a first preferred embodiment, shown in FIG. 3, there is provided a mandrel to cause the membrane to occupy a shape, when the membrane is fully contracted and the volume is substantially at zero, that the membrane would otherwise occupy when the system is filled with fluid to the point that the membrane first reaches the constant pressure mode. In this embodiment, the interior volume 14 is substantially zero when the membrane-containing system is devoid of fluid. In FIG. 3 membrane 31 is shown pretensioned, fully contracted and stretched over mandrel 32 so that the volume defined between the membrane and the mandrel is substantially zero. In FIG. 3, membrane 31 is supported in this initial (zero volume) position by mandrel 32 in substantially the same generally hemispherical shape that would have been occupied by the membrane had filled with fluid as shown in FIG. 1 to a volume 12, corresponding to the lower end of range B in FIG. 2.

The membrane 31 is thus mounted under tension around mandrel 32 and sandwiched between toroidal cap 321 and the foot 322 of the mandrel. In a typical preferred embodiment, the membrane provides a pressure of about five pounds per square inch (34 kPa) over its operating range. When the membrane is nearly fully expanded, it occupies the position identified as 31a, and defines interior volume 311. Case 33 provides a maximum limit on stretching of the membrane 31 and consequently on the size of volume 311.

The volume 331 between the membrane 31 and the case 33 is desirably vented in many applications to atmosphere to permit expansion and contraction of the membrane without compression and decompression of air in the volume 331. Venting may be achieved by any suitable means, including an orifice in case 33 or the creation of one or more channels between cap 321 and case 33; such channels could, for example, extend additionally between the foot 322 of mandrel 32 and the proximate portion of the case 33.

Initial filling of the system is achieved via luer fitting 34 and one-way valve 35. One suitable arrangement for implementing items 34 and 35 is disclosed in U.S. application Ser. No. 748,341, filed Aug. 22, 1991, entitled "Quick-Disconnect Valve," for an invention of Dean Kamen and Valentine Faust. That application is hereby incorporated herein by reference.

Fluid is dispensed by the system through channel 36 and fitting 37, which are integrally formed with mandrel 32. From the fitting 37, the fluid flow is through line 371, filter 38, and flow-restrictive tubing 39, though output fitting 391, which may be a luer fitting that is suitably capped until use of the system. The flow-restrictive tubing 39 has a specific and small cannula size so as to help assure constant pressure at the fitting 391 and provide a specified maximum flow rate through the fitting 391. The filter 38 provides filtering of the fluid and may also provide air elimination in manners known in the art. The line 371 may be clamped or otherwise modified to control flow in a manner known in the art. Alternatively, for example, flow can be controlled in a manner discussed in connection with FIG. 2 of the grandparent application Ser. No. 673,835, using technical approaches described in application Ser. No. 523,801 and in U.S. Pat. No. 4,976,162.

Figure 4:
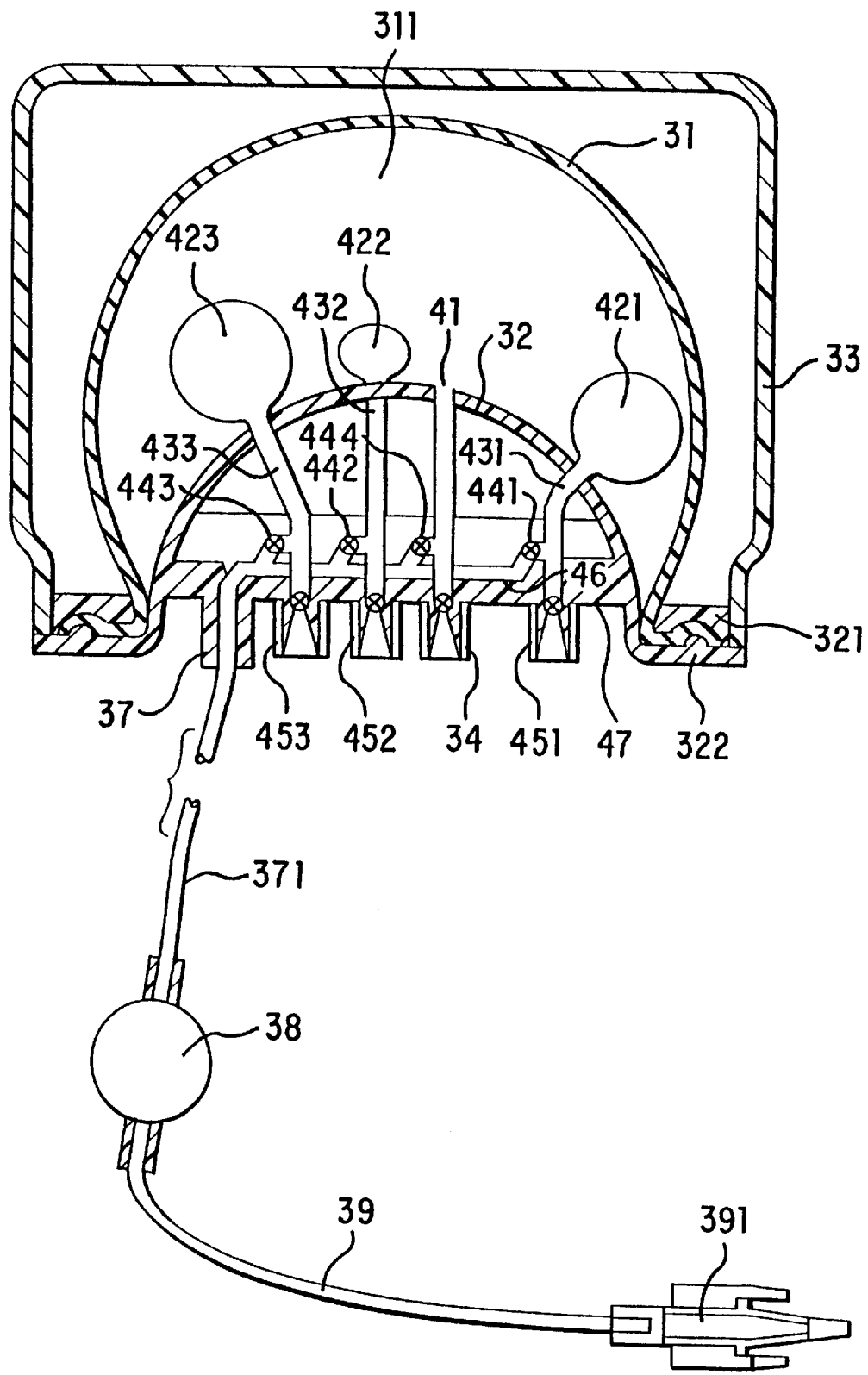
FIG. 4 is a cross section of a second embodiment of the invention having the capability of supply sequentially a series of fluids in any desired order.

FIG. 4 shows a system similar to that shown in FIG. 3 but capable of dispensing automatically in sequence a series of fluids in any desired order. In this embodiment, one fluid is placed in volume 311 defined by main membrane 31 and other fluids are placed in volumes 421, 422 and 423 defined by three additional membranes, which are disposed in the volume 311 between the main membrane 31 and the mandrel 32. The actual number of additional membranes is a matter of design choice, and here the three additional membranes are spaced at equal angles around the mandrel 32. The additional membranes are slack, i.e., they are not used in a stretched condition. Therefore, the pressure exerted by the stretching of the main membrane of the main interior volume is exerted equally on each additional interior volume defined by each additional (slack) membrane. Fluid may be dispensed from main volume 311 and from each additional 421, 422 and 423. Alternatively, fluid may be dispensed from the additional volumes only, the fluid in the main volume being used to provide the interior pressure. Fluids are loaded into the volumes 311, 421, 422 and 423 via fittings 34, 451, 452 and 453 respectively. One-way valves are provided in fluid communication with these fittings in the manner described in connection with FIG. 3, and the fluid input may be implemented as discussed in connection with FIG. 3 by techniques such as disclosed in the Quick-Disconnect Valve application referred to above or by means known in the art. For reasons to be discussed below, the first volume to be filled should be the one intended to be emptied first, the second volume to be filled should be the one intended to be emptied second, and so on; i.e., the volumes should be filled in the order that they are intended to be emptied.

The passageways from each of volumes 311, 421, 422 and 423 empty through one-way valves 444, 441, 442 and 443 respectively into manifold 46 that goes to the output fitting 37 and output line 371. These one-way valves will not pass fluid in the permitted direction until a specified pressure threshold is reached, and a different threshold is established for each valve. Such pressure-threshold one-way valves are known in the art, and may be implemented, for example, by duck-bill valves. The manifold 46, and the identified fittings and valves are here disposed in member 47, which is contiguous with mandrel 32.

It will be readily apparent that the pressure in volumes 421, 422 and 423 is the same as the pressure in volume 311. When fluid is permitted to flow through fitting 391, the fluid will flow through the one-way threshold valve 444, 441, 442 or 443 that has the lowest threshold. Assuming that such valve is valve 443, then once flow is established, the pressure from main membrane 31 is exerted to keep this valve open, and flow will continue until volume 423 has emptied completely and flow has ceased. Next, the threshold valve having the next lowest threshold opens, say, valve 442, and then its associated volume 422 empties completely, and so forth. Because of the geometry of the system, it is expected that volume 311 will be the last to empty, and desirably the threshold of its associated valve 444 is the highest.

A system of the general type described in FIG. 4 is applicable, among other things, to systems capable of delivering "SASH," i.e., in sequence, saline, antibiotic, saline and heparin. In order to assure against the possibility that medicine in a secondary volume such as 421, 422 or 423 is not completely emptied as for example by dislocation of its associated membrane, it may in some cases be desirable to establish enough secondary membranes, so that the main membrane may be loaded with a suitable sterile solution (such as saline) for dispensing last. In this manner the main membrane 31 will force to empty all the secondary membranes beneath it. Thus a SASH system would be implemented as a SASH-S system.

Although the multiple volume system of FIG. 4 has been described in connection with a single volume device according to FIG. 3 using a mandrel 32, it could in fact be implemented with prior art single volume system as well, using secondary volumes placed within the single main volume in a manner analogous to that described in connection with FIG. 4.

Figure 8:
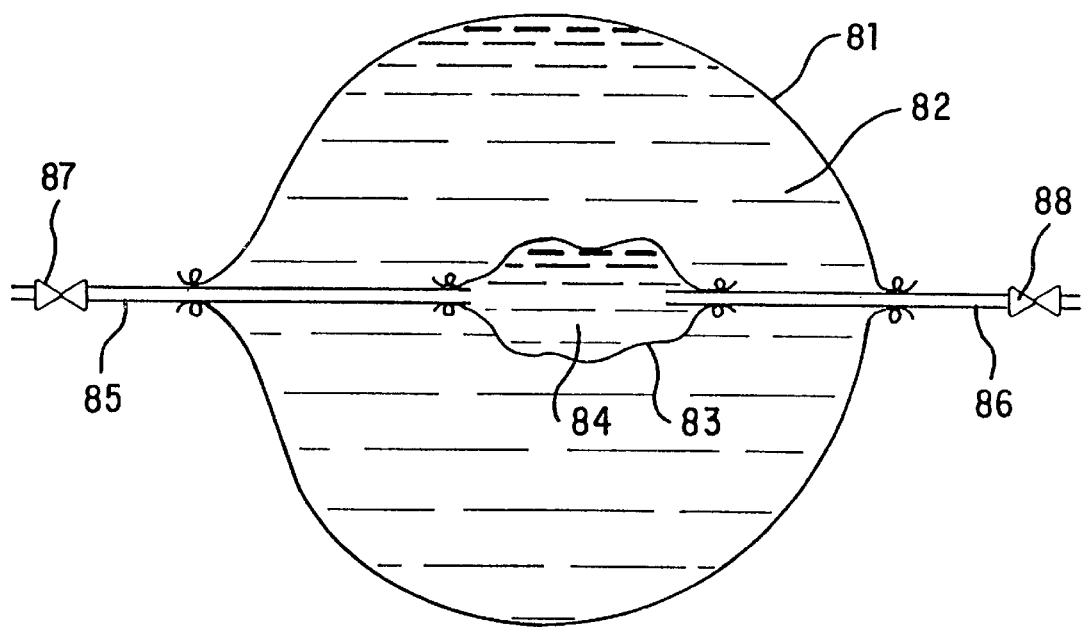
FIG. 8 illustrates a simple single-fluid delivery system using a resilient membrane and a dispensing membrane.

A simple system for delivery of a single fluid at a relatively constant pressure using a pressure chamber having an enclosed pressure fluid according to the present invention is shown in FIG. 8. A resilient membrane 81 encloses a pressure chamber filled with pressure fluid 82 such that membrane 81 is under tension. An additional slack membrane 83, within membrane 81, provides a dispensing chamber of varying dimension which may contain fluid 84, the fluid to be dispensed. A fluid input 85 and a fluid output 86 provide access for fluid 84 to enter and leave the dispensing chamber via valves 87 and 88 respectively. Pressure fluid 82 is sealed within the volume defined by membrane 81 (i.e., the pressure chamber of varying dimension) under pressure such that when the chamber containing fluid 84 is empty, membrane 81 is under tension corresponding to position 12 in FIG. 1. Because membrane 83 is a slack membrane, when the dispensing chamber contains fluid 84 (such as shown in FIG. 8), the pressure of fluid 84 is equal to the pressure of fluid 82. So, when valve 88 is opened, fluid 84, the fluid to be dispensed, is expelled under relatively constant pressure, corresponding to the pressure over range B in FIGS. 1 and 2.

Figure 5:
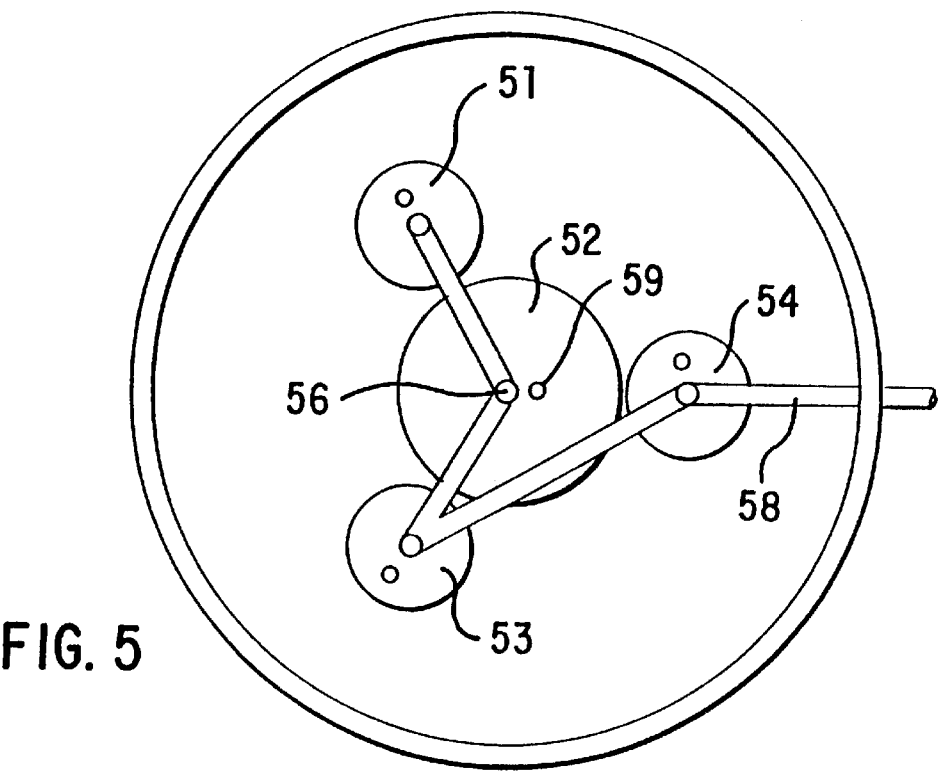
FIG. 5. is a schematic plan view of a third embodiment of the invention.
Figure 6:
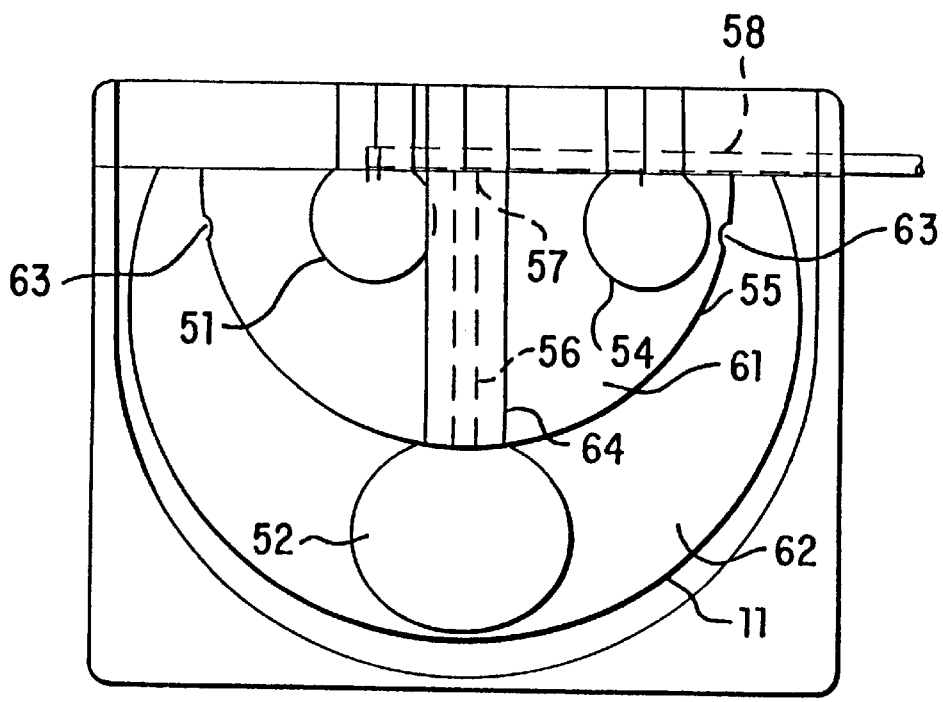
FIG. 6 is a schematic elevation view of the embodiment of FIG. 5.

FIGS. 5 and 6 show an embodiment similar to the embodiment of FIG. 4 except that fluid is dispensed only from the volumes (or "chambers") defined by additional membranes, not directly from the volume defined by the resilient membrane. Also, in the embodiment of FIGS. 5 and 6, three of the additional membranes 51, 53 and 54 are mounted inside volume 61 defined by the mandrel. (Additional membrane 52 is mounted between the resilient membrane and the mandrel.) In this embodiment, the pressure chamber includes the volume defined by the mandrel so that the pressure chamber fluid occupies volume 61 defined by the mandrel as well as volume 62 between mandrel 55 and resilient membrane 11. The mandrel has holes 63 in it to allow fluid to pass therethrough so that the pressure of fluid in the pressure chamber is exerted on the additional membranes inside the mandrel. The pressure chamber is filled with fluid and sealed prior to use. The embodiment of FIG. 5, which is 2.5 inches (6.4 cm) in diameter, accepts 24 cc of sterile water (non-dispensed fluid) for use solely to apply pressure to the dispensed fluids in each of the additional volumes. FIG. 5 is a schematic representation of four additional membranes 51, 52, 53 and 54, suitable for accepting SASH fluids. These four membranes are shown again, schematically, in FIG. 6, wherein membrane 53 is hidden directly behind membrane 51. Membrane 52 is shown on the central axis of mandrel 55 and its feed tube 56 extends through mandrel 55 to the spring-loaded valve associated with membrane 52 located in the region 57 and connected to manifold 58. Feed tube 56 and fill tube 59 run parallel to each other through feed post 64 to membrane 52. The fill tube access is a 1/16 inch (1.59 mm) diameter hole.

Figure 7:
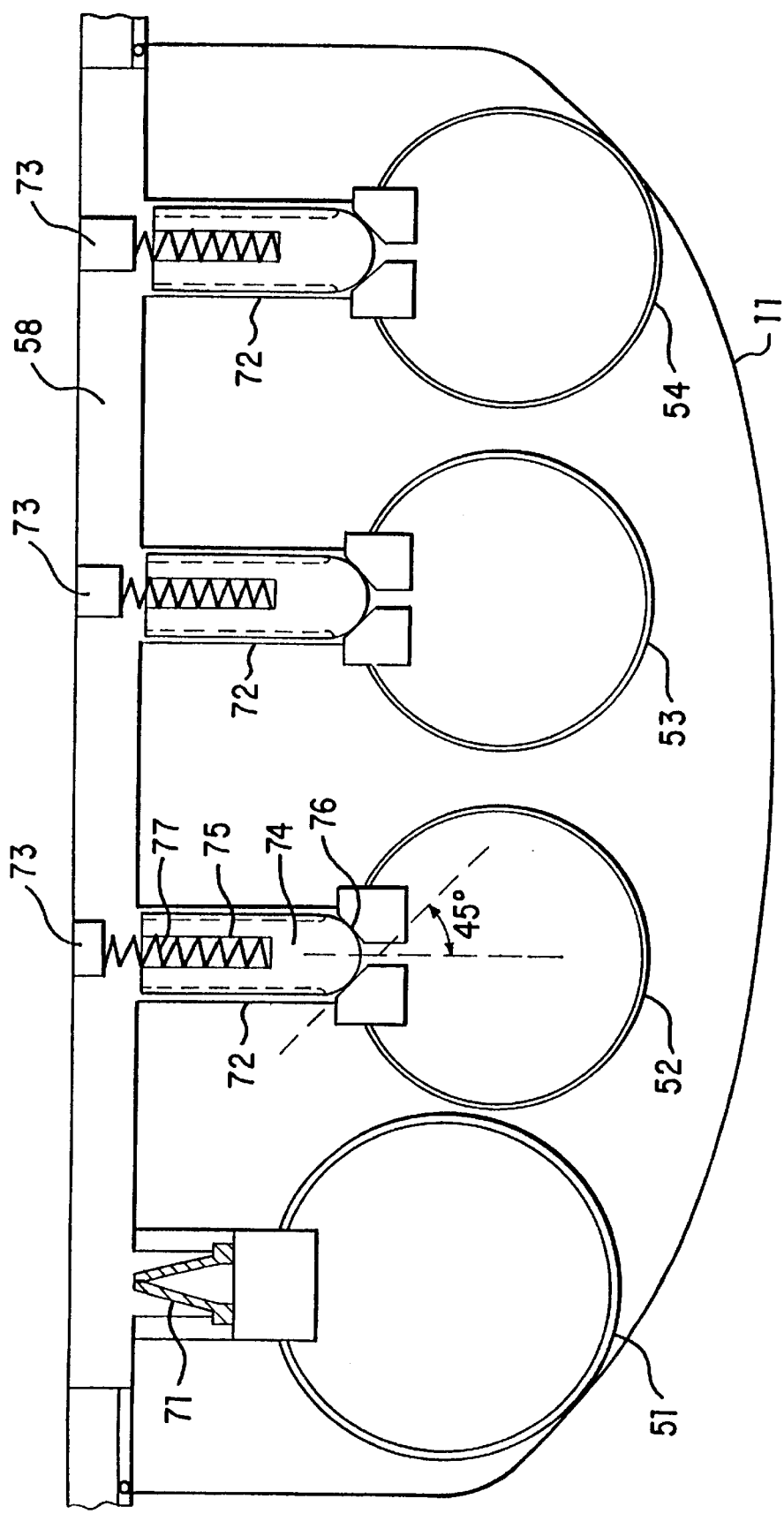
FIG. 7 is a schematic cross-section view of the digital valves of the embodiment of FIG. 5.

Returning now to FIG. 5, membranes 51, 52, 53 and 54 are seen to be connected in a line along manifold 58. The schematic of FIG. 7 shows membranes 51–54 enclosed by the resilient membrane 11 and schematically spread out in a line to illustrate the design principles. Membrane 51 is connected to the manifold via duck-bill valve 71. This valve opens first when the line to the patient (e.g., 371 in FIG. 4) is opened. Each of the downstream membranes 52, 53 and 54 is connected to the manifold via a spring-loaded digital valve 72. These valves are identical in construction except for the block 73 which sets the spring-force in its corresponding valve. It can be seen from FIG. 7 that a downstream block is larger than an upstream block. The larger block compresses the spring more, resulting in a greater force to be overcome to open the valve.

Each valve consists of a silicone rubber ball 74, having a spring slot 75, seated against a valve seat 76 and held in place by a spring 77 which is preloaded to the height of a block 73. Except for the blocks, each of which is molded into the cover and has a different height, the components of the valves are identical. Valve seat 76 is chamfered at 45° and the diameter of valve ball 74 is selected so that when it is seated, it defines an area such that the force due to fluid pressure (force=pressure×area) will be just sufficient to overcome the spring force and open the valve. The springs associated with membranes 52, 53 and 54 are preloaded by blocks 73 to provide a force of 6.5 oz (184 g), 11.9 oz (337 g) and 17.2 oz (488 g) respectively. The preload force is set by the height of the block. This wide variation of preload is necessary to ensure proper sequencing in spite of spring tolerances of ±10%.

It has been found beneficial not to have adjacent membranes touch because (i) this can interfere with the equalization of pressure within the system and (ii) a membrane might be pinched off, preventing it from fully discharging. Thus for a four-fluid (e.g., SASH) system the configuration of FIG. 5 is preferred, having three inner dispensing membranes 51, 53 and 54 and one outer dispensing membrane 52. The three inner dispensing membranes are sized not to touch each other. The outer non-dispensing pressure-producing membrane (resilient membrane 11) does not touch the outer dispensing membrane 52 by virtue of the size of membrane 52 and the amount of fluid in the sealed main volume being sufficient to prevent membrane 11 from contacting mandrel 55 when all dispensing membranes are empty. With dispensing membranes having 2–5 cc capacity, an additional 3 cc of main volume fluid is found to be sufficient.

What is claimed is:

1. A system for dispensing a liquid at relatively constant pressure, comprising:

a generally hemispherical mandrel having a curved portion and a foot;

a resilient membrane attached to the foot of the mandrel and stretched over the mandrel's curved portion, so as to provide a chamber of varying dimension between the membrane and the mandrel for holding the liquid, the resilient membrane having an inner face, exposed to the chamber, and an outer face, exposed to air; and a conduit for dispensing the liquid from the chamber;

wherein the mandrel and the membrane are attached so that the membrane is under tension regardless of the volume of the chamber, and so that, as the liquid is introduced into the chamber between the membrane and the mandrel, the shape of the membrane evolves from a generally hemispherical shape towards a generally spherical shape.

2. A system for dispensing a liquid at relatively constant pressure, comprising:

a generally hemispherical mandrel;

a resilient membrane attached to the mandrel under tension so as to provide a chamber of varying volume between the membrane and the mandrel for holding the liquid; and a conduit for dispensing the liquid from the chamber;

wherein the mandrel and the membrane are attached so that the membrane is under tension regardless of the volume of the chamber, so as to create a greater-than-ambient pressure within the volume, and wherein the resilient membrane is pre-tensioned beyond the point of smallest volume at which the first derivative of pressure over volume is zero.

3. A system for dispensing first and second liquids, comprising:

a resilient flexible membrane defining an outer chamber of varying volume, the membrane having an inner face, exposed to the outer chamber, and an outer face, exposed to ambient pressure;

wherein the first liquid is disposed in sufficient quantity within the outer chamber so as to stretch the resilient membrane and put it under tension, such that the resilient membrane under tension creates in the first liquid a greater-than-ambient pressure;

an inner chamber of varying dimension for containing the second liquid, the inner chamber being disposed within the outer chamber, so that the greater-than-ambient pressure created by the stretched membrane is imparted to the second liquid in the inner chamber;

a first conduit for dispensing the first liquid from the outer chamber;

a second conduit for dispensing the second liquid from the inner chamber;

an output manifold; and switch means, disposed between the output manifold and the first and second conduits, for serially permitting the liquids from the inner and outer chambers to flow into the output manifold;

wherein the membrane becomes less stretched as the liquids flow from the chambers.

4. A system according to claim 3, wherein the resilient membrane is pre-tensioned beyond the point of smallest volume at which the first derivative of pressure over total volume is zero.

5. A system according to claim 3, wherein the pressure in the chambers is substantially the same.

6. A system for dispensing different multiple fluids sequentially, comprising:

a resilient membrane defining a first volume of varying dimension for holding one of the multiple fluids;

at least one additional volume of varying dimension, disposed within the first volume, for holding another of the multiple fluids;

a first fluid conduit for dispensing fluid from the first volume;

a second fluid conduit for dispensing fluid from the additional volume;

an output manifold; and switch means, disposed between the output manifold and the fluid conduits, for serially permitting the fluids from the first volume and the additional volume to flow into the output manifold;

wherein the membrane is mounted so that, at all times when the first volume contains one of the multiple fluids, the resilient membrane is stretched, wherein the stretching of the membrane pressurizes the fluid in the first volume and the fluid in the additional volume, and wherein the membrane becomes less stretched as the liquids flow from the chambers.

7. A system according to claim 6, wherein the resilient membrane is pre-tensioned beyond the point of smallest volume at which the first derivative of fluid pressure over total fluid volume is zero.

8. A system according to claim 6 wherein the pressure in the volumes is substantially the same.

9. A system according to claim 6, wherein the switch means includes at least two compressed spring-loaded ball valves disposed in the conduits, wherein each spring-loaded ball valve requires a different force to be opened up.

10. A system according to claim 6, wherein the switch means includes a one-way threshold valve in fluid communication between the conduit of the first volume and the manifold and another one-way threshold valve between the conduit of the additional volume and the manifold.

11. A system according to claim 6, wherein the switch means includes at least one duck-bill valve between at least one of the conduits and the output manifold.

12. A system for dispensing multiple fluids sequentially, comprising:

a resilient membrane defining a first volume of varying dimension for holding one of the multiple fluids;

a fluid conduit for dispensing fluid from the first volume;

a plurality of additional volumes for holding one of the multiple fluids, wherein each of the additional volumes is of varying dimension and disposed within the first volume;

a plurality of fluid conduits for dispensing fluid from each of the additional volumes;

an output manifold; and switch means, disposed between the output manifold and the fluid conduits, for serially permitting the fluids from the first volume and the additional volumes to flow into the output manifold.

13. A system according to claim 12, wherein the switch means includes a one-way threshold valve in fluid communication between the conduit of the first volume and the manifold and between the conduit of each additional volume and the manifold.

14. A system according to claim 12, wherein the pressure in the volumes is substantially the same.

15. A system according to claim 12, wherein the switch means includes at least two compressed spring-loaded ball valves disposed in the conduits, wherein each spring-loaded ball valve requires a different force to be opened up.

16. A system according to claim 12, wherein the resilient membrane is pre-tensioned beyond the point of smallest volume at which the first derivative of fluid pressure over total fluid volume is zero.

17. A system according to claim 12, wherein the switch means includes at least one duck-bill valve between at least one of the conduits and the output manifold.

18. A system for dispensing multiple dispensable fluids sequentially, comprising:

a resilient membrane;

means for mounting the resilient membrane so as to provide a pressure chamber of varying dimension, and so as to stretch the resilient membrane and put it under tension;

at least two volumes of varying dimension for holding the dispensable fluids, each volume being disposed within the pressure chamber, each volume being in fluid communication with a fluid output;

an output manifold; and switch means, disposed between the output manifold and each of the fluid outputs, for serially permitting the fluids from the volumes to flow into the output manifold.

19. A system according to claim 18, wherein the resilient membrane is pre-tensioned beyond the point of smallest dimension at which the first derivative of fluid pressure over total fluid volume is zero.

20. A system according to claim 18 where the pressure in the volumes is substantially the same.

21. A system according to claim 18, wherein the switch means includes a one-way threshold valve in fluid communication between each of the fluid outputs and the manifold.

22. A device according to claim 18 wherein the means for mounting the resilient membrane includes a generally hemispherical mandrel having a curved portion and a foot, wherein the resilient membrane is attached to the foot of the mandrel and stretched over the mandrel's curved portion, so as to form the pressure chamber between the membrane and the mandrel, and so that as fluid is introduced into the pressure chamber, the shape of the membrane evolves from a generally hemispherical shape to a generally spherical shape.

23. A system according to claim 18, wherein the switch means includes at least two compressed spring-loaded ball valves disposed in the conduits, wherein each spring-loaded ball valve requires a different force to be opened up.

24. A system according to claim 18 wherein the switch means includes at least one duck-bill valve between at least one of the conduits and the output manifold.

25. A system for dispensing multiple dispensable fluids sequentially, comprising:

a resilient membrane;

means for mounting the resilient membrane so as to provide a pressure chamber of varying dimension;

at least two dispensable fluid chambers of varying dimension, each disposed within the pressure chamber, each having a fluid output;

an output manifold; and switch means for serially switching the outputs from the at least two dispensable chambers into the output manifold, wherein the fluid output includes a spring-loaded ball valve having a preload, and the switch means includes a post, disposed in the output manifold, the post sized and positioned such that the preload is in fixed relation to the height of the post.

26. A system according to claim 25, wherein the spring-loaded ball valve includes a ball seat having a chamfered face.

27. A system according to claim 25, wherein the pressure in the chambers is substantially the same.

28. A system for dispensing two dispensable fluids sequentially, comprising:

means for pressurizing a pressure chamber;

first and second volumes of varying dimension for holding the dispensable fluids, each volume being disposed within the pressure chamber so that the pressure within each of the two volumes is substantially the same;

an output manifold;

first and second fluid outputs providing fluid communication from first and second volumes respectively to the output manifold;

first and second one-way valves disposed in first and second fluid outputs respectively for preventing flow from the output manifold to the volumes and for permitting flow from the volumes to the output manifold when a pressure-differential threshold between the volume and the output manifold is reached, the first one-way valve having a smaller threshold than the second one-way valve so that fluid flows from the first volume to the output manifold before fluid flows from the second volume to the output manifold.

29. A device for pumping fluids which comprises:

a housing having a first fluid port, said housing being formed with a surface having a periphery and a predetermined contour circumscribed by said periphery; and an elastomeric membrane attached to said periphery over said contour surface to stretch said membrane into a nonlinear region of elasticity and create a potential chamber between said stretched membrane and said housing for receiving fluid therein through said first port and expelling fluid therefrom through a second port by nonlinear contraction of said membrane at a substantially constant pressure.

30. A device according to claim 29 wherein the surface having a periphery includes a generally hemispherical mandrel, and wherein the elastomeric membrane is attached to the mandrel and stretched over the mandrel, so as to form the potential chamber between the member and the mandrel.

31. A device according to claim 30, wherein the shape of the membrane evolves from a generally hemispherical shape to a generally spherical shape as fluid is introduced in the potential chamber.

32. A system for dispensing a liquid at relatively constant pressure, comprising:

a generally hemispherical mandrel;

a resilient membrane attached to the mandrel and stretched over the mandrel, so as to provide a chamber of varying dimension between membrane and the mandrel for holding the liquid; and a conduit for dispensing the liquid from the chamber;

wherein the mandrel and the membrane are attached so that the membrane is under tension regardless of the volume of the chamber; and so that, as the liquid is introduced into the chamber between the membrane and the mandrel, the shape of the membrane evolves from a generally hemispherical shape towards a generally spherical shape.

33. A system for dispensing a liquid at relatively constant pressure, comprising:

a generally hemispherical mandrel;

a resilient membrane attached to the mandrel under tension so as to provide a chamber of varying volume between the membrane and the mandrel for holding the liquid; and a conduit for dispensing the liquid from the chamber;

wherein the mandrel and the membrane are attached so that the membrane is under tension regardless of the volume of the chamber.

34. A system according to claim 33, wherein the shape of the membrane evolves from a generally hemispherical shape to a generally spherical shape as fluid is introduced to the chamber.

35. A system for dispensing first and second liquids, comprising:

a resilient flexible membrane defining an outer chamber of varying volume;

wherein the first liquid is disposed in sufficient quantity within the outer chamber so as to stretch the resilient membrane and put it under tension;

an inner chamber of varying dimension for containing the second liquid, the inner chamber being disposed within the outer chamber;

a first conduit for dispensing the first liquid from the outer chamber;

a second conduit for dispensing the second liquid from the inner chamber;

an output manifold; and first and second one-way valves disposed in first and second conduits respectively, the first one-way valve having a smaller threshold than the second one-way valve.

36. A system for dispensing first and second liquids, comprising:
- a resilient flexible membrane defining an outer chamber of varying volume;
- wherein the flexible membrane is stretched and put under tension;
- an inner chamber of varying dimension for containing the second liquid, the inner chamber being disposed within the outer chamber;
- a first conduit for dispensing the first liquid from the outer chamber;
- a second conduit for dispensing the second liquid from the inner chamber;
- an output manifold; and
- valve means, disposed between the output manifold and the first and second conduits, for serially permitting the liquids from the inner and outer chambers to flow into the output manifold.

37. A system according to claim 36, wherein the valve means includes at least one compressed spring-loaded ball valve disposed in at least one of the conduits, the spring-loaded ball valve requiring a predetermined force to open up.

38. A system according to claim 36, wherein the valve means includes a one-way threshold valve in fluid communication between the first conduit and the output manifold and another one-way threshold valve between the second conduit and the output manifold.

39. A system according to claim 36, wherein the valve means includes a duck-bill valve between at least one of the conduit and the output manifold.

40. A system for dispensing first and second liquids, comprising:
- a resilient flexible membrane defining an outer chamber of varying volume;
- an inner chamber of varying dimension for containing the second liquid, the inner chamber being disposed within the outer chamber;
- a first conduit for dispensing the first liquid from the outer chamber;
- a second conduit for dispensing the second liquid from the inner chamber;
- an output manifold; and
- first and second one-way valves disposed in first and second conduits respectively, the first one-way valve having a smaller threshold than the second one-way valve.

41. A system for dispensing first and second liquids, comprising:
- a resilient flexible membrane defining an outer chamber of varying volume;
- an inner chamber of varying dimension for containing the second liquid, the inner chamber being disposed within the outer chamber;
- a first conduit for dispensing the first liquid from the outer chamber;
- a second conduit for dispensing the second liquid from the inner chamber;
- an output manifold; and
- at least two compressed spring-loaded ball valves disposed in the first and second conduits respectively, wherein each spring-loaded ball valve requires a different force to be opened up.

42. A system for dispensing first and second liquids, comprising:
- a resilient flexible membrane defining an outer chamber of varying volume;
- an inner chamber of varying dimension for containing the second liquid, the inner chamber being disposed within the outer chamber;
- a first conduit for dispensing the first liquid from the outer chamber;
- a second conduit for dispensing the second liquid from the inner chamber;
- an output manifold; and
- at least one duck-bill valve between at least one of the conduits and the output manifold.

* * * * *